(12) United States Patent
Netzhammer

(10) Patent No.: US 10,981,200 B2
(45) Date of Patent: Apr. 20, 2021

(54) PROCESSING METHOD AND DEVICE FOR SMALL PARTS

(71) Applicant: Eric Netzhammer, Arlesheim (CH)

(72) Inventor: Eric Netzhammer, Arlesheim (CH)

( * ) Notice: Subject to any disclaimer, the term of this patent is extended or adjusted under 35 U.S.C. 154(b) by 53 days.

(21) Appl. No.: 16/081,710

(22) PCT Filed: Mar. 1, 2017

(86) PCT No.: PCT/EP2017/054803
§ 371 (c)(1),
(2) Date: Aug. 31, 2018

(87) PCT Pub. No.: WO2017/149029
PCT Pub. Date: Sep. 8, 2017

(65) Prior Publication Data
US 2019/0118228 A1    Apr. 25, 2019

(30) Foreign Application Priority Data
Mar. 2, 2016    (CH) .................................. 00268/16

(51) Int. Cl.
| | |
|---|---|
| *B08B 3/12* | (2006.01) |
| *F26B 5/02* | (2006.01) |
| *F26B 3/347* | (2006.01) |
| *F26B 9/06* | (2006.01) |
| *A61L 2/12* | (2006.01) |
| *B08B 3/04* | (2006.01) |
| *A61L 2/025* | (2006.01) |
| *A61L 2/07* | (2006.01) |
| *A61L 2/26* | (2006.01) |

(52) U.S. Cl.
CPC ................ *B08B 3/12* (2013.01); *A61L 2/025* (2013.01); *A61L 2/07* (2013.01); *A61L 2/12* (2013.01); *A61L 2/26* (2013.01); *B08B 3/04* (2013.01); *F26B 3/347* (2013.01); *F26B 5/02* (2013.01); *F26B 9/063* (2013.01); *A61L 2202/121* (2013.01); *A61L 2202/122* (2013.01); *A61L 2202/16* (2013.01); *A61L 2202/17* (2013.01); *A61L 2202/24* (2013.01)

(58) Field of Classification Search
None
See application file for complete search history.

(56) References Cited

U.S. PATENT DOCUMENTS

| | | | | |
|---|---|---|---|---|
| 3,445,092 | A | * 5/1969 | Melville, Jr. | ............. B08B 3/12 366/118 |
| 4,896,010 | A | 1/1990 | O'Connor et al. | |
| 5,759,486 | A | * 6/1998 | Peterson | .................... A61L 2/12 219/687 |
| 9,693,844 | B1 | * 7/2017 | Karapetyan | .......... A61C 19/002 |
| 2002/0159917 | A1 | * 10/2002 | Swart | .................... A61C 19/002 422/20 |

OTHER PUBLICATIONS

International Search Report for PCT/EP2017/054803 dated Oct. 20, 2017.

* cited by examiner

*Primary Examiner* — Cristi J Tate-Sims
(74) *Attorney, Agent, or Firm* — Birch, Stewart, Kolasch & Birch, LLP

(57) ABSTRACT

The processing device for small parts is equipped with ultrasound probes for decreasing the number of particles and with microwave generators for drying the small parts.

3 Claims, 1 Drawing Sheet

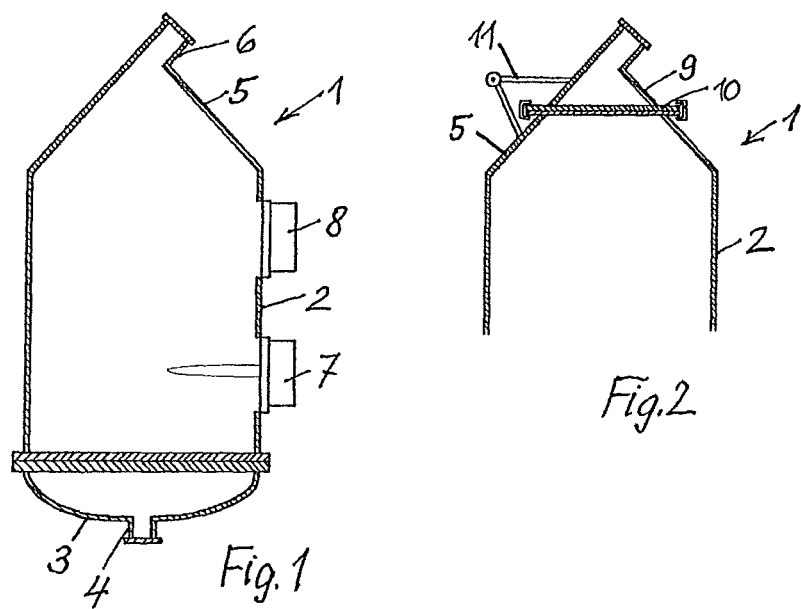
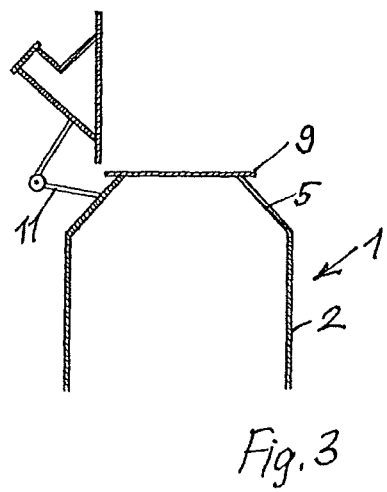

PROCESSING METHOD AND DEVICE FOR SMALL PARTS

The invention relates to a method and a device for conservational processing of bulk quantities of small parts in a container.

For the purpose of this description, the term "bulk quantities" refers to a quantity of small parts filled, that is, poured, in an unsorted manner, into a processing container, processed in the container, and then removed from the container, still unsorted. This type of the processing is for parts that are typically employed in the pharmaceutical or medical field, that is, parts of syringes, ampules, etc.

Consequently, for the purpose of this description, the term "small parts" relates to the unsorted individual parts of a bulk quantity, in particular small parts for use in the medical or pharmaceutical field.

In known devices for treating such small parts, the following quality-relevant standard processes are executed:
  Washing to decrease the number of particles, to decrease the number of endotoxins, to decrease the number of other substances (e.g. organic residual substances on the surface), etc.
  Sterilizing with steam to provide sterile parts
  Drying to reduce the residual moisture in the parts and on their surfaces.

For the washing process, the parts are dipped in water and air is blown onto them from below. This creates a so-called fluidized bed that moves the small parts and holds them in suspension. During this process, particles and other substances are washed out during and, using appropriate evacuation, with the water are separated from the small parts.

The known washing processes are able to decrease the number of particles and other substances, but often to an unsatisfactory extent. In particular, it is difficult to remove heavy particles, because the known processing machines can only be emptied from above. Since the small parts are employed in pharmaceutical and medical applications (e.g. injection ampules), decreasing the number of particles in particular is a critical quality feature.

In the known devices, drying of the small parts is accomplished using a vacuum and hot air.

The known drying processes are able to produce low residual moisture, which is medically often no longer adequate, however. On the one hand, residual water may be in the pores of the small parts, and this residual water may not be removed with the conventional processes. On the other hand, there may also be residual moisture on the surface. These residual moistures may have a profoundly negative impact on shelf-life, e.g. for lyophilized active substances. In addition, the drying time may take a number of hours until low residual moisture values are attained.

Another drawback of known processing devices is that, after one processing cycle and the emptying of the processing container, individual parts may remain in the container and consequently be processed multiple times. In particular, however, it is possible for different types of parts to be mixed, which may lead to problems in the subsequent machines.

The underlying object of the invention is to prevent or improve the aforesaid drawbacks of the prior art.

According to the invention, this is attained using a method and a device of the type identified in the foregoing that are distinguished by the characterizing features of claims 1 and 2.

The processing container is a rotating container that is rotatable in a cart or in a frame (prior art). Depending on what is required, it is provided with a filling option and a transfer system according to the prior art.

The container is equipped with one or a plurality of ultrasonic generates.

The container is equipped with a perforated sheet on which the small parts are disposed.

The container is filled with water so that the ultrasonic generator and parts are completely submerged. The parts are now cleaned with ultrasound.

Once the cleaning has been accomplished, the water level is reduced so that the heavy particles can move downward and leave the processing container. Then the liquid level is raised until there is an overflow so that the light particles are removed.

The container is equipped with one or a plurality of microwave generators. The small parts are dried using microwaves.

Ultrasound cleaning and microwave drying may be combined, or may even just be used individually. This depends, inter alia, on the nature of the material for the parts.

Preferred exemplary embodiments of the invention are described in the following using the attached drawings.

FIG. 1 is a sectional schematic diagram of an inventive processing device;

FIG. 2 is a sectional schematic diagram of another form of an inventive processing device, shown closed;

FIG. 3 is a sectional schematic diagram of the processing device illustrated in FIG. 2, shown open here.

The processing container 1 illustrated in FIG. 1 has a cylindrical side wall 2, known per se, having an attached flange-like arched bottom 3. A perforated sheet (not shown) is also arranged in the region of the flange in a manner known per se. An inlet connection 4 for processing media is disposed in the bottom. At the other end of the container, connected to the side wall is a conical region 5 at which an inlet and outlet connection for the small parts 6 to be processed is disposed.

Arranged on the side wall is an ultrasound generator 7 that acts on the container contents with ultrasound waves to clean the container contents better.

In addition, arranged on the side wall is a microwave generator 8 that, after the cleaning phase, acts on the container contents with microwaves to promote drying of the container contents.

In the processing container illustrated in FIGS. 2 and 3, a part 9 of the conical region is connected to the container by means of a flange 10 and a hinge device 11. The flange is embodied in a manner known per se such that it may be released easily. In this way the aforesaid part 9 of the conical region of the container may be flipped open, as shown in FIG. 3, to form an opening sufficiently large for manual inspection. The processed parts may also be emptied through this opening, since the container is rotatably borne on a cart.

The invention claimed is:

1. A device for conservational processing of bulk quantities of small parts filled in an unsorted manner into a processing container, the container being rotatable in a cart or in a frame and having a lower portion with a cylindrical side wall and a conical region having an upper portion constituting an inlet and outlet region, comprising one or a plurality of additional devices arranged on the cylindrical side wall of the container, the additional devices including one or a plurality of ultrasound probes or one or a plurality of microwave generators, and wherein the conical region consists of a lower and an upper part which are connected by a flange to each other and the two parts each are connected to a hinge device such that the upper part may be completely flipped open from the container.

2. The processing device according to claim 1, characterized in that the container has an arched bottom in which is arranged an inlet connection for processing media.

3. The processing device according to claim 1, characterized in that the part of the conical region that can be flipped open is provided with an inlet and outlet connection for the parts to be processed.

* * * * *